United States Patent [19]

Sircar et al.

[11] 4,247,555

[45] Jan. 27, 1981

[54] 4,9-DIHYDRO-9-OXO-N-1H-TETRAZOL-5-YL-PYRAZOLO[5,1-b]-QUINAZOLINE-2-CARBOXAMIDES AND ANTIALLERGIC COMPOSITIONS AND METHODS USING THEM

[75] Inventors: Jagadish C. Sircar, Ann Arbor; Thomas Capiris, Plymouth, both of Mich.

[73] Assignee: Warner-Lambert Company, Morris Plains, N.J.

[21] Appl. No.: 111,147

[22] Filed: Jan. 11, 1980

Related U.S. Application Data

[63] Continuation-in-part of Ser. No. 6,046, Jan. 24, 1979, abandoned.

[51] Int. Cl.$^3$ .................. A61K 31/505; C07D 487/14
[52] U.S. Cl. ..................................... 424/251; 544/250
[58] Field of Search .......................... 544/250; 424/251

[56] References Cited

U.S. PATENT DOCUMENTS

| | | | |
|---|---|---|---|
| 3,150,136 | 9/1964 | Wolfram et al. | 544/250 |
| 3,157,655 | 11/1964 | Takamizawa et al. | 544/281 |
| 3,167,537 | 1/1965 | Menzel et al. | 544/250 X |
| 3,887,559 | 6/1975 | Hardtmann | 544/250 |
| 4,017,625 | 4/1977 | Kadin | 424/251 |
| 4,033,961 | 7/1977 | Schwender et al. | 544/252 |
| 4,112,098 | 9/1978 | Vogt | 424/251 |

OTHER PUBLICATIONS

Menzel et al., Chemical Abstracts, vol. 56, 4904g, (1962).

*Primary Examiner*—Donald G. Daus
*Assistant Examiner*—D. Rivers
*Attorney, Agent, or Firm*—Stephen I. Miller; Stephen Raines; Albert H. Graddis

[57] ABSTRACT

Certain 4,9-dihydro-9-oxo-N-1H-tetrazol-5-yl-pyrazolo[5,1-b]quinazoline-2-carboxamides are disclosed. These compounds prevent the allergic response in mammals.

12 Claims, No Drawings

4,9-DIHYDRO-9-OXO-N-1H-TETRAZOL-5-YL-PYRAZOLO[5,1-B]-QUINAZOLINE-2-CARBOXA-MIDES AND ANTIALLERGIC COMPOSITIONS AND METHODS USING THEM

CROSS REFERENCE TO RELATED APPLICATION

This application is a continuation-in-part of our pending application Ser. No. 006,046, filed Jan. 24, 1979, now abandoned.

BACKGROUND OF THE INVENTION

U.S. Pat. Nos. 3,150,136 and 3,167,537 disclose, inter alia certain pyrazoloquinazolone carboxylic acids which are useful as intermediates for the preparation of dyestuffs. German Pat. No. 1,111,505 discloses substituted 2-carboxy-pyrazolo-[5,1-b]quinazolin-9(4H)-ones which are useful as photographic color developers. The references do not disclose any pharmaceutical utility for these acids, nor do they disclose the carboxamido tetrazoles of the present invention.

SUMMARY OF THE INVENTION

The present invention relates to a compound of the formula I:

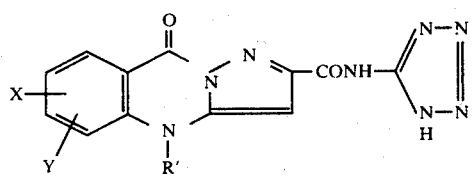

wherein X is hydrogen, hydroxy, alkyl of from 1 to 6, carbon atoms, alkoxy of from 1 to 6 carbon atoms, halo, trifluoromethyl, or $SO_nR$ wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; R' is hydrogen or alkyl of from 1 to 6 carbon atoms and the pharmaceutically acceptable salts thereof.

The invention also relates to a pharmaceutical composition comprising an anti-allergic effective amount of a compound of the formula I, and the pharmaceutically acceptable salts thereof.

The invention also relates to a method of preventing the allergic response in a mammal which comprises administering to said mammal an anti-allergic effective amount of a compound of formula I and the pharmaceutically acceptable salts thereof.

DESCRIPTION OF THE INVENTION

The compounds of the invention of the formula I:

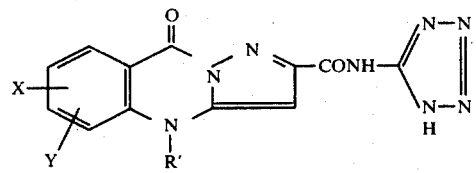

wherein X, Y and R' are as defined above may be prepared from the corresponding acids of formula II

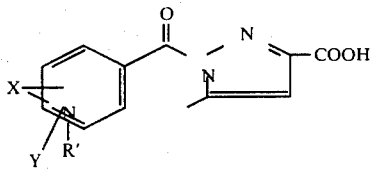

by methods familiar to those skilled in the art. For example, the properly substituted carboxylic acid may be converted to the corresponding acid halide such as the chloride by treatment with thionyl chloride or oxalyl chloride. Treatment of the halide with 5-aminotetrazole produces the compounds of formula I. Alternatively, a carboxylic acid of formula II may be treated with 1,1-carbonyl-diimidazole to produce a compound of formula III.

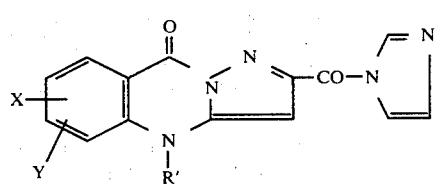

Treating the so produced compound of formula III with 5-aminotetrazole, for example in dimethylformamide solution, will produce the corresponding carboxamidotetrazole of formula I. Those skilled in the art will recognize that the intermediate carbonylimidazole of formula III need not be isolated prior to being treated with 5-aminotetrazole. In addition, the properly substituted carboxylic acid of formula II may be directly coupled with 5-aminotetrazole by use of such agents as N-ethoxycarbonyl-2-ethoxy-1,2-dihydroquinoline (EEDQ), dicyclohexylcarbodiimide (DCC) and the like.

The required carboxylic acids of formula II may be prepared by alternate procedures, which are considered equivalent for purposes of the invention. In one such procedure a 3-alkoxycarbonyl-2-pyrazolin-5-one having formula IV

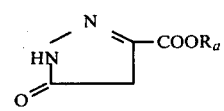

wherein $R_a$ is any convenient alkyl group, preferably of from 1 to 6 carbon atoms, most preferably ethyl is reacted in the presence of a strong base such as sodium hydride with a substituted N-alkyl isatoic anhydride of formula V

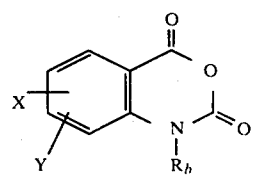

wherein X and Y are as defined above, and $R_b$ is alkyl of from 1 to 6 carbon atoms producing a 4-alkyl-4,9-dihydro-9-oxo-pyrazolo[5,1-b]quinazoline-2-carboxylic acid ester having formula VI

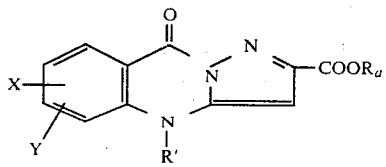

wherein X, Y, $R_a$ and $R_b$ are as defined above. The ester function of the compound of formula VI may be hydrolyzed by any convenient procedure to produce the corresponding acid, i.e., the compound of formula II wherein R' is alkyl of from 1 to 6 carbon atoms.

The 3-alkoxycarbonyl-2-pyrazolin-5-ones of formula IV may be prepared by the procedure of R. V. Rothenberg, J. Prakt, Chem., 2, 53 (1895).

The substituted N-alkyl isatoic anhydrides of formula V may be prepared by the procedure of G. E. Hardtmann, et al., J. Hetero. Chem., 12, 565 (1975); these compounds may also be prepared by alkylating the corresponding N-unsubstituted isatoic anhydride which themselves may be prepared for example, by reacting a properly substituted anthranilic acid with phosgene. Several of these compounds are also commercially available from the Aldrich Chemical Company, Milwaukee, Wis. and the Sherwin Williams Company, Cleveland, Ohio.

The alkylthio anthranilic acids which are utilized to prepare the corresponding alkylthio substituted isatoic anhydrides are novel, and may themselves be prepared by alternate procedures which are considered equivalent for purposes of the invention. One such procedure involves the steps of treating a halo-substituted 2-nitrobenzoic acid with sodium sulfide; alkylating the so produced mercaptan; followed by reduction of the nitro group thereby producing the desired alkylthio substituted anthranilic acid. The above-described alkylated mercaptan may also be produced by treating the halo-substituted 2-nitrobenzoic acid with a mercaptide such as a sodium mercaptide. The starting halo-substituted 2-nitrobenzoic acids are either commercially available or may be prepared by methods known to those skilled in the art. For example, 5-chloro-2-nitrobenzoic acid is available from Aldrich Chemical Company, Milwaukee, Wis. 53233. J. Pharm. Soc. Japan, 72, 76 (1952), [C.A.: 46, 1150h (1952)] discloses ethyl 5-ethylthio anthranilate.

In an alternate procedure, a 2-carboxy(or 2-carboalkoxy)pyrazolo[5,1-b]quinazoline-9(4H)-one of the formula VII

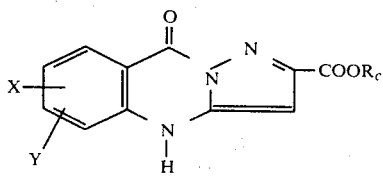

wherein X and Y are as defined above and $R_c$ is hydrogen or alkyl of from 1 to 6 carbon atoms may be alkylated by standard procedures to produce the corresponding 4-alkyl derivative. the compounds of formula VII may be prepared for example, by converting the above-described N-unsubstituted isatoic anhydrides to the corresponding 2-aminobenzoic acid hydrazide by treatment with aqueous hydrazine hydrate solution. The hydrazide is next converted to the desired 2-carboxypyrazolo[5,1-b]quinazolin-9(4H)-one by treatment with diethyl oxalacetate sodium salt.

The compounds of the invention of formula I are acidic in nature and form pharmaceutically acceptable salts with both organic and inorganic bases such as dimethylaminoethanol, the alkali metal and alkaline earth hydroxides and the alkali metal carbonates and bicarbonates such as lithium, sodium, potassium and calcium hydroxide, and the carbonates and bicarbonates of lithium, sodium and potassium. The salts are prepared by reacting the tetrazole with the desired base in the conventional manner. The carboxamido tetrazoles differ from their respective salts somewhat in certain physical properties such as solubility in polar solvents, but the salts are otherwise equivalent to their respective carboxamido tetrazoles for purposes of the invention.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The alkylthio groups, alkoxy groups and alkyl groups contemplated by the invention comprise both straight and branched carbon chains of from 1 to 6 carbon atoms. Representative of such groups are methyl, ethyl, isopropyl, pentyl, 3-methylpentyl, methoxy, ethoxy, propoxy, 1-ethylbutoxy, pentoxy, methylthio, isopropylthio, n-butylthio and the like. The term halo is intended to include fluorine, chlorine, bromine and iodine.

The compounds of the invention of formula I are new chemical substances of value as pharmacological agents which prevent the allergic response in mammals by inhibition of the release of such allergic mediators, as histamine. The assay by which this utility was established is carried out as follows.

Rat Reaginic Passive Cutaneous Anaphylaxis (PCA)

The PCA test (D. J. Herzig, P. R. Schumann, E. J. Kusner, L. Robichaud, R. E. Giles, B. Dubnick, M. von Strandtmann, S. Klutchko, M. Cohen, and J. Shavel, Jr., "Immunopharmacology", M. E. Rosenthale and H. C. Mansmann, Eds., Spectrum Publications, Inc., New York, N.Y., 1975, pp. 103-124) involved immunization of rats with 1 mg of ovalbumin intramuscularly and approximately $10^{10}$ B. pertussis organisms as pertussis vaccine, intraperitoneally. Fourteen days layer, the rats were bled and the serum was prepared. Suitable dilutions of antiserum were injected intradermally at various sites on the back of rats 48 hrs before an intravenous injection of 1 mg of ovalbumin in 1 ml of physiological saline and 0.25% Evans Blue. Thirty minutes later the animals were killed in ether, the dorsal skin was reflected, and the mean orthogonal diameter of the wheal was measured. For oral or intraperitoneal dosing, the drugs were suspended in 1% gum tragacanth in physiological saline and given 10-15 min before intravenous antigen challenge. For intravenous dosing, the compounds were dissolved in the saline/ovalbumin/Evans Blue solution and given with the antigen. If necessary, the compounds were first dissolved in a slight molar excess of sodium bicarbonate and then diluted into the antigen solution. Groups of five animals were used for all dose levels and control groups.

To quantitate the PCA test, the mean diameter of each wheal spot was graphed as a function of the relative anti-serum concentration. The line, fitted by the least-squares equation, was extrapolated to the value at "zero" antiserum concentration (base value). The following equation was then used to calculate the percent inhibition:

$$\% \text{ inhibition} = \left[1 - \left(\frac{\text{diameter of drug} - \text{base value}}{\text{diameter of control} - \text{base value}}\right)\right] \times 100$$

The statistical significance of the results was determined by Student's t test ($p \leq 0.05$). An inhibition of 15% was significant.

The compositions of the invention can be administered in a variety of dosage forms such as tablets or capsules and liquids for oral or parenteral use. The dosage forms may contain, in addition to the active component, any of the usual compounding excipients such as flavors, colors, stabilizers and tableting materials such as binders, fillers, lubricants and the like. The dosage requirements may vary with the particular composition being employed and may depend on the severity of the symptoms being presented and the size of the mammal being treated. In general, an amount of from about 0.1 to about 10 mg/kg of the active component in single or divided doses will be sufficient to accomplish the method of the invention.

The invention is illustrated by the following examples.

EXAMPLE 1

4,9-Dihydro-4-methyl-9-oxo-N-1H-tetrazol-5-yl-pyrazolo[5,1-b]quinazoline-2-carboxamide.

To a warm mixture of 4-methyl-4,9-dihydro-9-oxo-pyrazolo[5,1-bZ]quinazoline-2-carboxylic acid (0.19 g; 0.0078 mole) in dimethylformamide (50 ml) is added, 1,1'-carbonyl-diimidazole (2.78 g; 0.0172 mole) and the mixture is heated at 100° C. for 15 min. 5-Aminotetrazole monohydrate (0.88 g; 0.0086 mole) is then added to the hot solution and the heating continued for another 2.5 hours. The reaction mixture is cooled to 50° C., the solid is filtered and washed successively with methanol and ether and dried. Yield 2.4 g; mp 338°–340° C. The sodium salt is prepared by mixing the product with an equivalent amount of 0.1 N aqueous sodium hydroxide solution with warming to cause the product to dissolve, evaporating the water off and drying the sodium salt product in vacuum. The potassium, calcium and magnesium salts are prepared by the same procedure.

EXAMPLE 2

4,9-Dihydro-5-methoxy-9-oxo-N-1H-tetrazol-5-yl-pyrazolo[5,1-b]quinozoline-2-carboxamide.

To a suspension of 1-[4,9-dihydro-5-methoxy-9-oxo-pyrazolo-[5,1-b]-quinazolin-2-yl-carbonyl]-1H-imidazole in dimethylformamide is added a mixture of 5-aminotetrazole monohydrate (1 eq.) and 1,1'-carbonyl-diimidazole (1.1 eq.) in dimethylformamide and the mixture is stirred at 100° C. for 2 hrs when the product slowly crystallizes out; mp 280°–285° C. (d).

EXAMPLE 3

4,9-Dihydro-7-methylthio-9-oxo-N-1H-tetrazol-5-yl-pyrazolo[5,1-b]quinazoline-2-carboxamide with 1H-imidazole (1:1), hydrate (4:5).

1,1'-carbonyldiimidazole (1.46 g; 9.0 mmole) is added to a warm (90°) suspension of 4,9-dihydro-7-methylthio-9-oxo-pyrazolo[5,1-b]quinazoline-2-carboxylic acid (1.1 g; 4 mmole) in DMF (40 ml) 5-amino-1H-tetrazole monohydrate (0.46 g; 4.5 mmole) is added and the solution is heated @ 90° for 3.5 hrs. The product crystallizes out on cooling. Yield 0.5 g; mp 285° (d).

EXAMPLE 4

4,9-Dihydro-7-[(1-methylethyl)thio]-9-oxo-N-1H-tetrazol-5-yl pyrazolo[5,1-b]quinazoline-2-carboxamide with 1H-imidazole (4:1).

From 4,9-dihydro-7-[(1-methylethyl)thio]-9-oxo-pyrazolo[5,1-b]quinazoline-2-carboxylic acid (0.91 g; 3 mmole), 1,1'-carbonyldiimidazole (1.1 g; 6.8 mmole), DMF (20 ml) and 5-amino-1H-tetrazole, monohydrate (0.35 g; 3.4 mmole) following the procedure of Example 3, there is obtained 4,9-dihydro-7-[(1-methylethyl)thio]-9-oxo-N-1H-tetrazol-5-yl-pyrazolo[5,1-b]quinazoline-2-carboxamide with 1H-imidazole (4:1) (0.8 g); mp > 300° (d).

EXAMPLE 5

4,9-Dihydro-7-butylthio-9-oxo-N-1H-tetrazol-5-yl-pyrazolo[5,1-b]quinazoline-2-carboxamide, with 1H-imidazole (3:1).

From 4,9-dihydro-7-butylthio-9-oxo-pyrazolo-[5,1-b]quinazoline-2-carboxylic acid (1.9 g; 6 mmole), DMF (25 ml), 1,1'-carbonyl-diimidazole (2.19 g; 13.5 mmole) and 5-amino-1H-tetrazole, monohydrate (0.70 g; 6.8 mmole), following the procedure of Example 3, there is obtained 4,9-dihydro-7-butylthio-9-oxo-N-1H-tetrazol-5-yl-pyrazolo[5,1-b]quinazoline-2-carboxamide, with 1H-imidazole (3:1) (0.4 g); mp 285° (d).

EXAMPLE 6

4,9-Dihydro-5,7-dimethoxy-9-oxo-N-1H-tetrazol-5-yl-pyrazolo[5,1-b]quinazoline-2-carboxamide.

From 4,9-dihydro-5,7-dimethoxy-9-oxo-pyrazolo-[5,1-b]quinazoline-2-carboxylic acid (1.54 g; 5 mmole), DMF (300 ml), 1,1'-carbonyldiimidazole (1.8 g; 11 mmole) and 5-amino-1H-tetrazole, monohydrate (0.52 g; 5 mmole), following the procedure of Example 3, there is obtained 4,9-dihydro-5,7-dimethoxy-9-oxo-N-1H-tetrazol-5-yl-pyrazolo-[5,1-b]quinazoline-2-carboxamide (0.78 g); mp 338°–342° (d).

EXAMPLE 7

4,9-Dihydro-9-oxo-5-(tetrahydro-2-thienyl)-N-1H-tetrazol-5-yl-pyrazolo[5,1-b]quinazoline-2-carboxamide.

From 4,9-dihydro-9-oxo-5-(tetrahydro-2-thienyl)-pyrazolo[5,1-b]quinazoline-2-carboxylic acid, compound with methanol (1:1) (0.40 g; 1.3 mmole), DMF (20 ml); 1,1' carbonyl-diimidazole (0.5 g; 3.1 mmole) and 5-amino-1H-tetrazole, monohydrate (0.131 g; 1.3 mmole), following the procedure of Example 3, there is obtained 4,9-dihydro-9-oxo-5-(tetrahydro-2-thienyl)-N-1H-tetrazol-5-yl-pyrazolo[5,1-b]quinazoline-2-carboxamide (70 mg); mp > 230° (d).

EXAMPLE 8

4,9-Dihydro-7-(methylsulfinyl)-9-oxo-N-1H-tetrazol-5-yl-pyrazolo[5,1-b]quinazoline-2-carboxamide with pyridine (4:3).

From 4,9-dihydro-7-(methylsulfinyl)-9-oxo-pyrazolo-[5,1-b]quinazoline-2-carboxylic acid (1.40 g; 5 mmole), DMF (50 ml), 1,1'-carbonyl-diimidazole (2.43 g; is mmole) and 5-amino-1-H-tetrazole, monohydrate (0.62 g; 6 mmole), following the procedure of Example 3, there is obtained 4,9-dihydro-7-(methylsulfinyl)-9-oxo-N-1H-tetrazol-5-yl-pyrazolo[5,1-b]quinazoline-2-carboxamide with pyridine (4:3), mp>350°; after crystallization from pyridine-ether.

EXAMPLE 9

Following the procedure of Example 1, the following compounds are prepared:

| X | Y | R' | mp °C. | Solvent of Recrystallization or Wash Solvent |
|---|---|---|---|---|
| (a) H | H | H | 315-330°(d) | Methanol |
| (b) 7-Cl | H | H | >360° | Acetic Acid |
| (c) 5-CH₃O | H | H | 280-285°(d) | DMF |
| (d) 5-CH₃ | H | H | 290-5°(d) | CH₂Cl₂ |
| (e) 7-OH | H | H | >295°(d) | DMF—MeOH |
| (f) 7-CH₃O | H | H | 335°(d) | MeOH—Et₂O |
| (g) 8-CH₃O | H | H | 340-4°(d) | DMF |
| (h) 6-CH₃O | 7-CH₃O | H | 290-5°(d) | Acetic Acid |

PREPARATIVE EXAMPLES

Preparative Example 1

1-(4,9-Dihydro-5-methoxy-9-oxo-pyrazolo[5,1-b]-quinazolin-2-yl-carbonyl)-1H-imidazole.

To a warm (75° C.) solution of 4,9-dihydro-5-methoxy-9-oxo-pyrazolo[5,1-b]quinazoline-2-carboxylic acid (0.52 g) in dimethylformamide (100 ml) is added 1,1'-carbonyl-diimidazole (0.49 g) and the mixture heated at 85° C. for 15 min when slowly a yellow solid crystallizes out. Yield 0.24 g; mp 295°–300° C.

We claim:

1. A compound of the formula I:

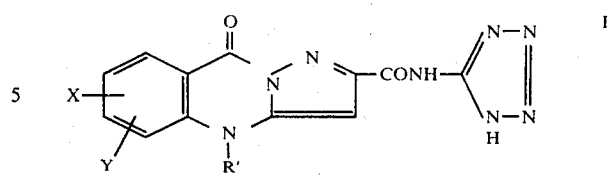

wherein X is hydrogen, hydroxy, alkyl of from 1 to 6 carbon atoms, alkoxy of from 1 to 6 carbon atoms, halo, trifluoromethyl, or SO$_n$R wherein R is alkyl of from 1 to 6 carbon atoms and n is 0, 1 or 2; Y is hydrogen, hydroxy, alkyl of from 1 to 6 carbon atoms, alkoxy of from 1 to 6 carbon atoms, or 2-tetrahydrothienyl; R' is hydrogen or alkyl of from 1 to 6 carbon atoms and the pharmaceutically acceptable salts thereof.

2. The compound as defined in claim 1 which is 4,9-dihydro-9-oxo-N-1H-tetrazol-5-yl-pyrazolo[5,1-b]quinazoline-2-carboxamide and the pharmaceutically acceptable salts thereof.

3. The compound as defined in claim 1 which is 4,9-dihydro-5-methoxy-9-oxo-N-1H-tetrazol-5-yl-pyrazolo[5,1-b]quinazoline-2-carboxamide and the pharmaceutically acceptable salts thereof.

4. The compound as defined in claim 1 which is 4,9-dihydro-8-methoxy-9-oxo-N-1H-tetrazol-5-yl-pyrazolo[5,1-b]quinazoline-2-carboxamide and the pharmaceutically acceptable salts thereof.

5. The compound as defined in claim 1 which is 4,9-dihydro-7-methoxy-9-oxo-N-1H-tetrazol-5-yl-pyrazolo[5,1-b]quinazoline-2-carboxamide and the pharmaceutically acceptable salts thereof.

6. The compound as defined in claim 1 which is 4,9-dihydro-5-methyl-9-oxo-N-1H-tetrazol-5-yl-pyrazolo[5,1-b]quinazoline-2-carboxamide and the pharmaceutically acceptable salts thereof.

7. The compound as defined in claim 1 which is 4,9-dihydro-6,7-dimethoxy-9-oxo-N-1H-tetrazol-5-yl-pyrazolo[5,1-b]quinazoline-2-carboxamide and the pharmaceutically acceptable salts thereof.

8. The compound as defined in claim 1 which is 4,9-dihydro-7-hydroxy-9-oxo-N-1H-tetrazol-5-yl-pyrazolo[5,1-b]quinazoline-2-carboxamide and the pharmaceutically acceptable salts thereof.

9. The compound as defined in claim 1 which is 4,9-dihydro-7-methylthio-9-oxo-N-1H-tetrazol-5-yl-pyrazolo[5,1-b]quinazoline-2-carboxamide and the pharmaceutically acceptable salts thereof.

10. 4,9-Dihydro-4-methyl-9-oxo-N-1H-tetrazol-5-yl-pyrazolo[5,1-b]quinazoline-2-carboxamide.

11. A pharmaceutical composition comprising an anti-allergic effective amount of a compound as defined in claim 1 and the pharmaceutically acceptable salts thereof.

12. A method of preventing the allergic response in a mammal which comprises administering to said mammal an anti-allergic effective amount of a composition as claimed in claim 11.

* * * * *